United States Patent [19]

Letterio

[11] 4,438,773
[45] Mar. 27, 1984

[54] SUBARACHNOID BOLT

[75] Inventor: Fred Letterio, Philadelphia, Pa.

[73] Assignee: Paul L. Sweeney, Jr., Laurel Springs, N.J.

[21] Appl. No.: 358,444

[22] Filed: Mar. 15, 1982

[51] Int. Cl.³ .................................................. A61B 5/00
[52] U.S. Cl. .................................... 128/748; 128/303 R
[58] Field of Search ............... 128/748, 303 R, 303 B; 604/93

[56] References Cited

U.S. PATENT DOCUMENTS 4,062,354 12/1977 Taylor et al. ................. 128/748 X
4,186,728 2/1980 Van Lofringen ............. 128/748 X

FOREIGN PATENT DOCUMENTS 2384482 11/1978 France ................................. 128/748
7801416 9/1978 Netherlands ....................... 128/748

Primary Examiner—Lee S. Cohen
Assistant Examiner—Angela D. Sykes
Attorney, Agent, or Firm—Duffield & Lehrer

[57] ABSTRACT

A subarachnoid bolt for use in measuring intracranial pressure includes a lower bolt half and an upper bold half which can be screwed into the lower bolt half. A tubular member extends downwardly from the lower bolt half and is adapted to be inserted into a hole formed in a patient's skull. The bolt is securely held in place when the free end of a tubular element carried by the upper bolt half enters the tubular member and cams the lowermost end thereof radially outwardly when the two bolt halves are screwed together.

6 Claims, 4 Drawing Figures

SUBARACHNOID BOLT

BACKGROUND OF THE INVENTION

The present invention is directed toward a subarachnoid bolt for use in measuring intracranial pressure.

Subarachnoid bolts for measuring or monitoring intracranial pressure have been known for some time. One of the more widely utilized bolts, commonly referred to as a "Philly" bolt, is comprised essentially of stainless steel or similar material and includes an external screw thread at its lower end which is intended to be screwed into a twist drill hole formed in a patient's skull. The extreme end of the bolt enters the subarachnoid space over the cerebral hemisphere.

While known subarachnoid bolts have met with some success, they have also suffered from many problems particularly with patients with very thin skulls such as neonatal patients. With such patients and in many other cases, it is extremely difficult and sometimes impossible to secure the bolt to the skull by screwing the same thereto.

SUMMARY OF THE INVENTION

The present invention overcomes the defects of the prior art known to Applicant and provides a subarachnoid bolt which can be easily secured to substantially any skull. The bolt of the present invention includes a lower bolt half and an upper bolt half which can be screwed into the lower bolt half. A tubular member extends downwardly from the lower bolt half and is adapted to be inserted into a hole formed in a patient's skull. The bolt is securely held in place when the free end of a tubular element carried by the upper bolt half enters the tubular member and cams the lowermost end thereof radially outwardly when the two bolt halves are screwed together.

BRIEF DESCRIPTION OF THE DRAWING

For the purpose of illustrating the invention, there is shown in the accompanying drawing one form which is presently preferred; it being understood that the invention is not intended to be limited to the precise arrangements and instrumentalities shown.

DETAILED DESCRIPTION OF THE PREFERRED EMBODIMENT

Figure 1:
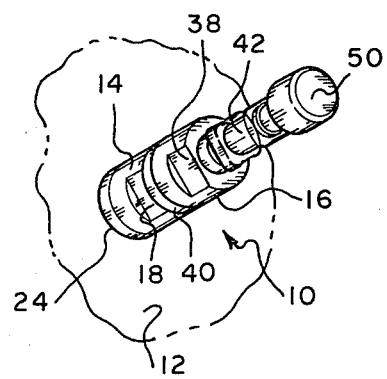
FIG. 1 is perspective view of a subarachnoid bolt constructed in accordance with the principles of the present invention.

Referring now to the drawing in detail wherein like reference numerals have been used throughout the various figures to designate like elements, there is shown in FIG. 1 a subarachnoid bolt constructed in accordance with the principles of the present invention and designated generally as 10. In FIG. 1, bolt 10 is shown secured to the skull 12 of a patient.

Bolt 10 is comprised essentially of two parts: A lower bolt half 14 and an upper bolt half 16. As shown most clearly in FIGS. 2 and 3, lower bolt half 14 is essentially circular in cross section except for the upper portion thereof which is squared as shown at 18 to form a means by which a wrench or similar tool can hold the lower bolt half 14 to prevent the same from rotating. The reason for this will become more readily apparent hereinafter.

The lower section of lower bolt half 14 is reduced in diameter and forms a tubular member 20 which is coaxially aligned with the remaining parts of the bolt. An enlarged flange 22 is thereby formed above the tubular member 20. A sealing washer 24 rests against the flange 22 and around the upper part of the tubular member 20.

Figure 3:
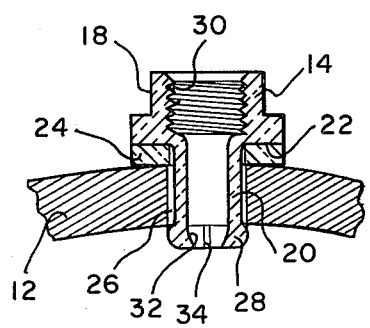
FIG. 3 is a cross-sectional view of the lower bolt half inserted in a hole in a patient's skull.

As shown most clearly in FIG. 3, the tubular member 20 is adapted to be inserted into a substantially complementary shaped hole 26 in a patient's skull 12. The length of the tubular member 20 is selected so that the lowermost end 28 thereof which is slightly bulbous lies just below the lowermost surface of the skull 12. The flange 22 and washer 24 overlie the outer surface of the skull 12 around the hole 26.

Lower bolt half 14 is substantially hollow, having a channel passing entirely therethrough. An internal screw thread 30 is formed in the uppermost part and the inner surface of the lowermost end 28 is substantially conically shaped as shown at 32. The wall of the lowermost end 28 of the tubular member 20 also includes a plurality of axially extending slits 34 therein. In the preferred embodiment of the invention, four such slits are shown (see FIG. 2). This is by way of example only as the invention could function with fewer or more such slits. The purpose of the slits 34 is to weaken the wall of the lowermost end portion 28 slightly so that the same can be flexed outwardly when the bolt is in use as will be explained more clearly hereinafter. With the end portion 28 flexed outwardly, the bulbous portion forces against the undersurface of the skull 12 to retain the bolt in place.

Figure 2:
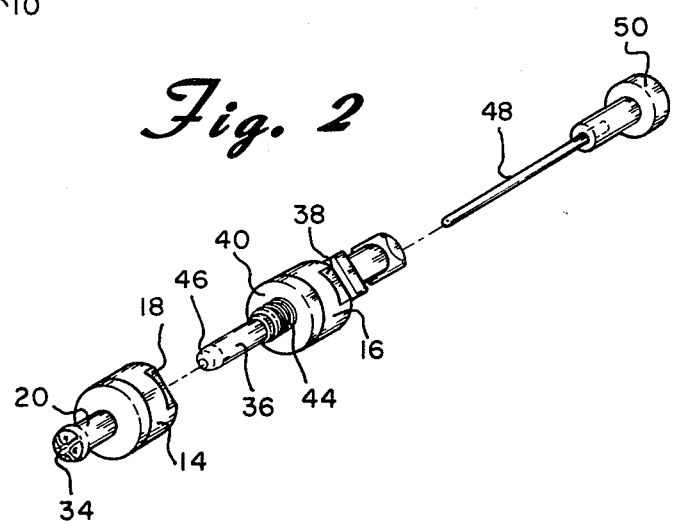
FIG. 2 is an exploded perspective view of the bolt shown in FIG. 1.
Figure 4:
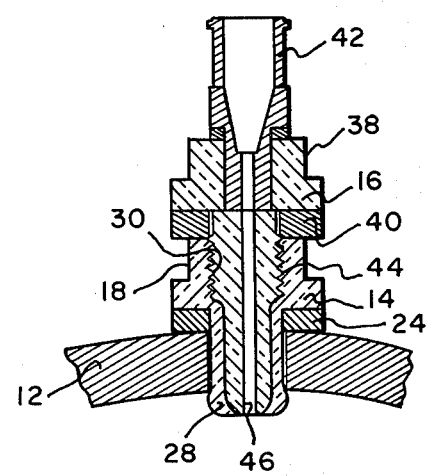
FIG. 4 is a cross-sectional view of the bolt secured to a patient's skull.

The details of the upper bolt half 16 are shown most clearly in FIGS. 2 and 4. As with the lower bolt half 14, the upper bolt half 16 has a main body portion with a concentrically arranged tubular element 36 extending downwardly therefrom. A squared section 38 similar to section 8 also allows the upper bolt half to be held by a wrench or similar tool so that the same can be turned relative to the lower bolt half. A washer 40 similar to washer 24 extends around the uppermost part of the tubular element 36. The uppermost part of the upper bolt half 16 carries a coaxially arranged adapter or connector 42 which is utilized for connecting the bolt to remotely located sensing and/or measuring equipment.

An external screw thread 44 is formed on the upper end of the tubular element 36. This screw thread 44 is complementary to the screw thread 30 on the lower bolt half 14 so that the two bolt halves can be secured together with the tubular element 36 entering the interior of the lower bolt half 14. The forwardmost end 46 of the tubular element 36 is also substantially conically shaped and as the two bolt halves are screwed together, this end 46 moves downwardly and pushes against the conical inner surface 32 to cam the lower end 28 of the lower bolt half 14 outwardly to secure the bolt in place. A conventional pin 48 with handle 50 may also be utilized to seal the interior of the bolt 10 whenever the same is not being utilized for measuring intracranial pressure.

Bolt 10 is used in the following manner. A hole 26 is first drilled in the patient's skull 12 at the appropriate position. Bolt halves 14 and 16 are separated and tubular member 20 of bolt half 14 is passed through the bolt 26 with the bulbous end 28 lying just below the surface of the skull 12 and the washer 24 and flange 22 lying above the skull for sealing the same. The tubular element 36 of the upper bolt half 16 is then inserted into the interior of the lower bolt half 14. A wrench is then used to hold the lower bolt half 14 while a second wrench or similar tool is used to turn the upper bolt half 16 so that the two bolt halves are threaded together. Eventually, the lowermost end 46 of the tubular element 36 will function as a cam to flex the lowermost end 28 of the tubular member 20 outwardly to secure the bolt in position on the skull as shown in FIG. 4.

Any suitable materials may be utilized in the manufacture of the bolt 10. In the preferred embodiment, the adapter 42 is comprised of stainless steel or the like while the remaining parts of the bolt are preferably made of a relatively rigid plactic. The washers are, of course, preferably comprised of a somewhat softer material so that they will produce the desired sealing function.

The present invention may be embodied in other specific forms without departing from the spirit or essential attributes thereof and accordingly, reference should be made to the appended claims rather than to the foregoing specification as indicating the scope of the invention.

I claim:

1. A subarachnoid bolt for use in measuring intracranial pressure including:
    a lower bolt half having a top, an enlarged flange and a coaxially arranged tubular member extending downwardly from said flange, said tubular member being adapted to be inserted into a substantially complementary shaped hole in a patient's skull with said flange overlying the outer surface of the skull around said hole, said tubular member having a lowermost end which is radially expandable so that the same is adapted to be secured to the patient's skull;
    means on said lower bolt half for allowing the same to be held to prevent rotation thereof;
    an upper bolt half screwed to the top of said lower bolt half, said upper bolt half having a downwardly extending tubular element fitted within said tubular member of said lower bolt half when said upper and lower bolt halves are screwed together.

2. The invention as claimed in claim 1 wherein said tubular element has a leading end and the lowermost end of said tubular member is made to expand radially by said leading end.

3. The invention as claimed in claim 2 wherein the lowermost end of said tubular member includes a plurality of axially extending slits in the wall thereof.

4. The invention as claimed in claim 2 wherein the lowermost end of said tubular member has an outer configuration which is slightly bulbous.

5. The invention as claimed in claim 2 wherein the lowermost end of said tubular member has an inner surface which is substantially conically shaped and functions as a cam surface.

6. The invention as claimed in claim 1 wherein said lower bolt half has an upper surface and an opening therein which is concentric with said tubular member and which has an internal screw thread therein and wherein said tubular element includes an upper end and a complementary external screw thread on said upper end.

* * * * *